United States Patent [19]

Kaufman

[11] 4,312,362
[45] Jan. 26, 1982

[54] SINGLE SAMPLE NEEDLE WITH VEIN ENTRY INDICATOR

[75] Inventor: Joseph Kaufman, Emerson, N.J.

[73] Assignee: Becton, Dickinson and Company, Paramus, N.J.

[21] Appl. No.: 193,054

[22] Filed: Oct. 2, 1980

[51] Int. Cl.³ .............................................. A61B 5/14
[52] U.S. Cl. ................................... 128/763; 128/771
[58] Field of Search .............................. 128/763–771, 128/218 NV

[56] References Cited

U.S. PATENT DOCUMENTS

| | | | |
|---|---|---|---|
| 3,585,984 | 6/1971 | Buchanan | 128/276 X |
| 3,817,240 | 6/1974 | Ayres | 128/771 |
| 3,886,930 | 6/1975 | Ryan | 128/771 |
| 4,166,450 | 9/1979 | Abramson | 128/764 |
| 4,207,870 | 6/1980 | Eldridge | 128/766 |

*Primary Examiner*—John D. Yasko
*Attorney, Agent, or Firm*—Richard J. Rodrick

[57] ABSTRACT

A needle assembly preferably suitable for single sample blood collection and for determining vein entry when collecting a blood sample from a patient into a vacuum collection device. This assembly includes a housing with an interior chamber with a blood inlet needle on one side of the housing and a blood outlet needle on the other. The outlet needle extends interiorly into the chamber, is closed at the end and includes a pair of holes each spaced preferably along an axial line. A slidable plug is operatively positioned in the chamber to prevent liquid from flowing into the side holes while allowing gas to flow into at least one of the side holes at a first position in the chamber whereby the prevented liquid may be viewed by a user through a transparent portion of the housing. The operative plug is movable to a second position in the chamber to allow liquid to flow into at least one of the side holes whereby liquid may be collected from the outlet needle of the assembly.

22 Claims, 7 Drawing Figures

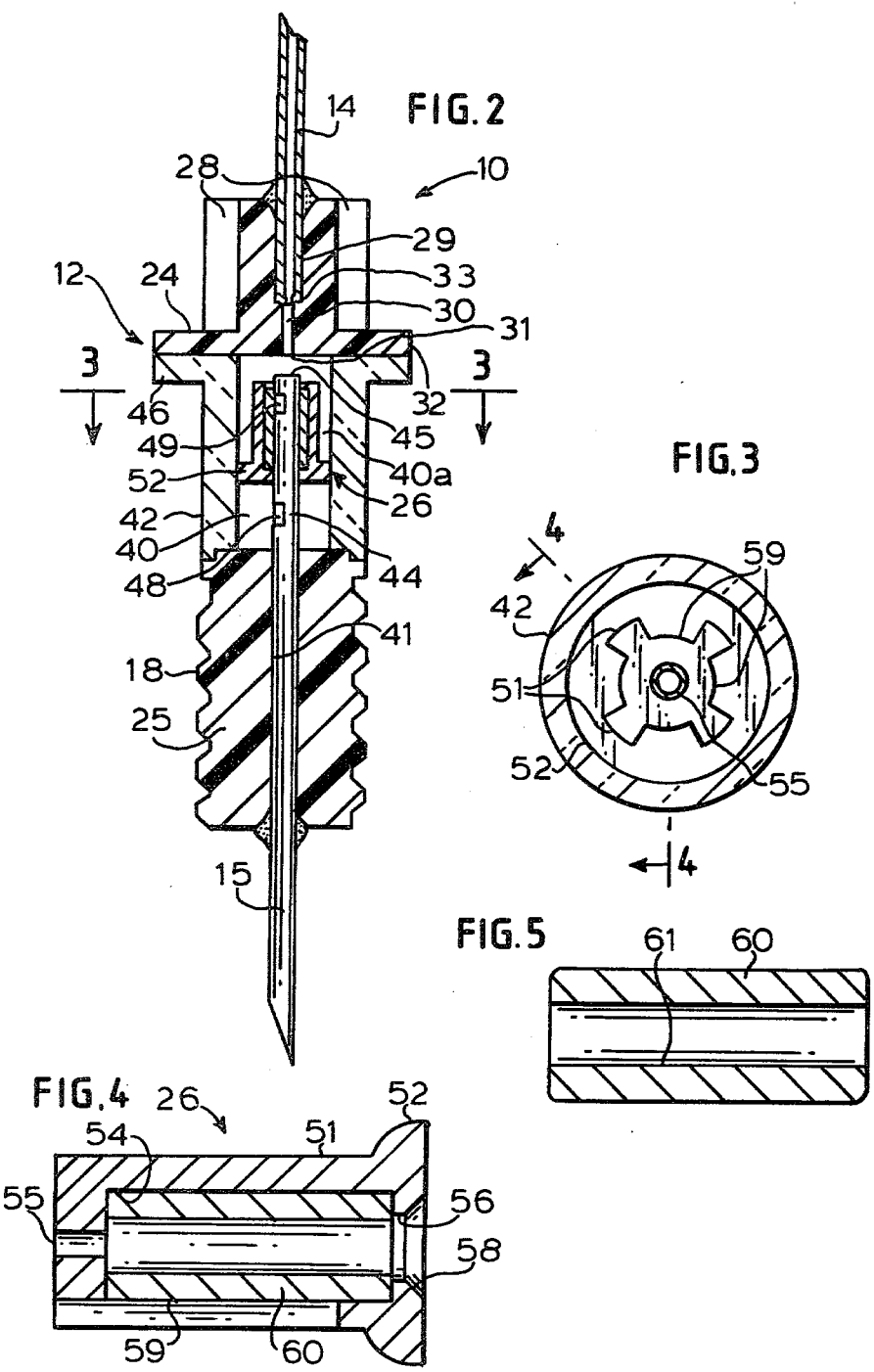

SINGLE SAMPLE NEEDLE WITH VEIN ENTRY INDICATOR

BACKGROUND OF THE INVENTION

1. Field of the Invention

The present invention relates to a needle assembly for collecting fluid from a patient, and more particularly, concerns a needle assembly for collecting a single sample of blood from a patient while providing an indication of entry of the needle assembly into the vein of the patient.

2. Description of the Prior Art

In the collection of body fluids, such as blood from a patient, the nurse or clinician collecting this fluid oftentimes must probe for or guess the location of the patient's vein. For instance, the nurse attempting to collect a blood sample, even with tourniquet pressure applied, cannot readily insert the needle in patients who have small veins or if the veins are somewhat removed from the skin surface. In those instances, the needle may either miss the vein entirely or perhaps may pass completely through a thin vein. As a result, blood flow through the needle into the evacuated blood collection tube would be uncomfortable and inefficiently slow since the blood would not be flowing from the patient's vein. The nurse would have to start over again and perhaps use another evacuated blood collection tube on the next attempt, which, of course, would be wasteful of both materials and expense, not to mention the discomfiture which the patient experiences.

In order to reduce the waste of evacuated blood collection tubes which occurs in the blood collecting procedure where the nurse must guess at vein location, a number of blood collecting devices have been proposed which provide an indicator to the user that satisfactory vein entry has been accomplished. In these visual indicator devices, an antechamber is generally provided which is kept isolated by some sort of valving mechanism from the opening of the needle which deposits the blood being collected into the evacuated tube. Once the nurse probes for the vein and satisfactory entry is made, blood is supposed to flow through the needle into the antechamber to provide a telltale trace that the vein has been properly located. At this point in the blood collecting procedure, an evacuated blood collection tube is then usually inserted into the blood collection holder, opening up some type of valve whereby blood is then free to flow into the evacuated blood collection tube. Typical of these visual indicator blood collection devices are those found in U.S. Pat. Nos. 4,166,450 and 3,585,984.

Although, in theory, this antechamber approach for the telltale trace of blood flow is workable, and oftentimes may work satisfactorily, there are, nevertheless, some inherent problems with this approach. For example, the antechamber generally is filled with air at the time the forward end of the needle is inserted into the vein of the patient. Inasmuch as the opposite end of the needle, for puncturing the evacuated blood collection tube, is valved or closed, the air in the antechamber forms a blockage since there is no place for such air to be displaced. Thus, even if the nurse locates the vein, and satisfactory entry is made with normal tourniquet pressure, the blood flow from the patient may not travel all the way through the needle before reaching the antechamber. This is due to the fact that the air in the antechamber blocks the blood flow through the needle even under normal tourniquet pressure. The net result of this is that the nurse will be deceived into believing that satisfactory vein entry has not been accomplished since no telltale trace will be visually observed. Unnecessary secondary venipuncture may take place, which, again, is not only uncomfortable to the patient, but is inefficient and wasteful.

Accordingly, improved approaches for providing a visual indicator to the user of a blood collecting device are still being sought. These improvements are needed in those types of blood collecting devices which make entry into the vein of the patient before the evacuated blood collection tube is inserted into the blood collection holder, which now is a very common blood collecting procedure.

SUMMARY OF THE INVENTION

A needle assembly for determining fluid access when collecting a fluid sample from a source of fluid into a vacuum collection device comprises a housing with a chamber therein and having first and second access means therethrough in fluid communication with the chamber. The housing includes means for viewing the contents inside the chamber, with the second access means adapted for fluid communication with a vacuum collection device. Means extends into the chamber for directing passage of gas and liquid into the second access means. Means operatively plugs the chamber to prevent liquid from flowing into the extension means while allowing gas to flow into the extension means at a first position in the chamber. The prevented liquid may be viewed by a user through the viewing means. The operative plug means is movable to a second position in the chamber to allow liquid to flow into the extension means whereby liquid may be collected from the second access means.

In a preferred embodiment of the needle assembly of the present invention as generally set forth above, the housing is translucent and has a forward end, a rearward end and a chamber within. A first cannula extends outwardly from the forward end of the housing in fluid communication with the chamber. A second cannula has an exterior portion extending outwardly from the rearward end of the housing and also has an interior portion extending inwardly into the chamber with a closed end and a pair of spaced side holes therethrough, preferably in axial alignment. A composite plug of air-permeable, blood-impermeable material and an elastomeric generally impermeable material is slidably positioned in the chamber with the impermeable material forming an outer envelope around the air-permeable material. A plurality of openings extends through the impermeable material so that the air-permeable material is in direct fluid communication with the chamber. The impermeable material is in liquid-tight contact with the housing surrounding the chamber and the interior portion of the second cannula. Initially, the plug overlies the side hole in the second cannula more distal to the rearward end of the housing while leaving the other side hole uncovered inside the chamber. Thus, any blood, but not air, flowing into the chamber from the first cannula under normal tourniquet pressure is prevented by the plug from flowing into the second cannula but can be viewed by a user through the translucent housing to indicate vein entry by the first cannula. The composite plug is adapted to slide under the influence of a negative pressure gradient applied to the second cannula to thereby uncover the distal side hole and move toward the other side hole. Accordingly, blood may flow into the chamber, through the distal side hole and then through the second cannula for collection into the blood collection container.

In accordance with the principles of the present invention, there are structural elements and features herein which are notably different from prior inventions of this type. For instance, the plug material inside the chamber serves as a valve mechanism to prevent blood from flowing out of the chamber when the patient needle has been inserted into the vein of the patient. At this point of the blood collecting procedure, the evacuated blood collection tube is normally not yet in position. Therefore, at this point blood should not be allowed to escape from the needle assembly. However, once the nurse makes entry into the patient's vein, blood will flow through the forward needle and enter the chamber inside the needle assembly. The nature of the plug material being essentially blood-impermeable will prevent any blood flow through the chamber. However, this same plug material is air-permeable so that any air either initially in the chamber or in the forward needle will be allowed to escape from the chamber and needle assembly to eliminate the blockage which occurs in prior art needle assemblies proposed for visual indicator operation. Moreover, the plug material is slidable within the chamber so that when the evacuated blood collection tube is attached to the other side of the needle assembly, the negative pressure gradient will cause the plug to slide inside the chamber thereby exposing one of the preferred side holes in the collection cannula to the blood flow path. In this fashion, as soon as the evacuated blood collection tube is attached, the plug moves to effect a valve opening thereby allowing the blood to flow through the needle assembly and into the blood collection container.

Advantageously, the present invention eliminates the deficiencies of the air blockage problem as set forth above with respect to prior art needle assemblies. In this regard, the present invention allows the user to visually observe the trace of blood entering into the chamber inside the needle assembly as soon as the vein has been properly entered, since any air inside the needle assembly is allowed to escape, thereby permitting the free flow of blood into the chamber.

BRIEF DESCRIPTION OF THE DRAWINGS

FIG. 2 is an enlarged cross-sectional view taken along line 2—2 of FIG. 1;

FIG. 3 is an end view of the preferred composite plug for use in the chamber of the embodiment of FIG. 1 taken along line 3—3 of FIG. 1;

FIG. 4 is a cross-sectional view taken along line 4—4 of FIG. 3;

FIG. 5 is a cross-sectional view similar to the view of FIG. 4 but only depicting the air-permeable, blood-impermeable material of the composite plug illustrated in FIG. 3;

DESCRIPTION OF THE PREFERRED EMBODIMENT

Figure 1:
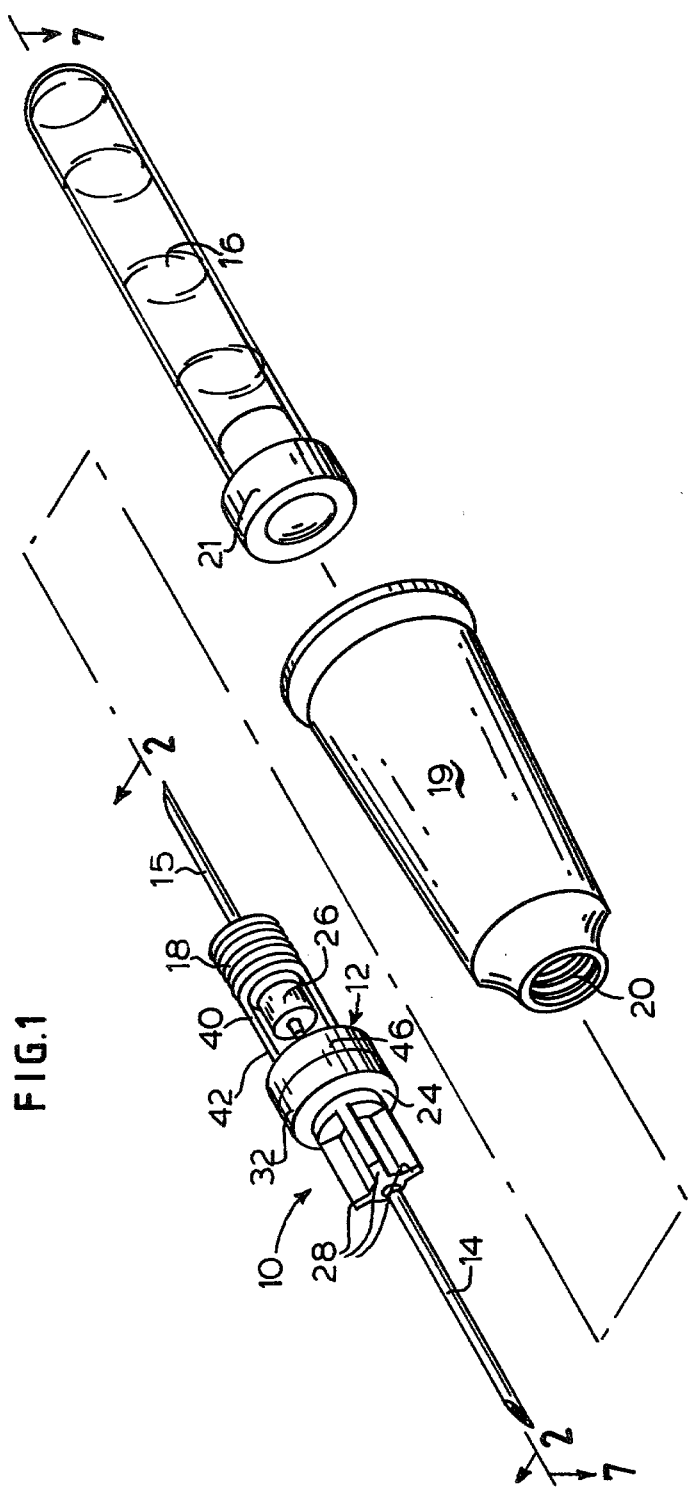
FIG. 1 is an exploded perspective view illustrating the preferred single sample needle assembly, a holder for an evacuated container and an evacuated blood collection container for use in obtaining a blood sample from a patient.

While this invention is satisfied by embodiments in many different forms, there is shown in the drawings and will herein be described in detail a preferred embodiment of the invention, with the understanding that the present disclosure is to be considered as exemplary of the principles of the invention and is not intended to limit the invention to the embodiment illustrated. The scope of the invention will be measured by the appended claims and their equivalents.

Adverting to the drawings, particularly FIG. 1, there is illustrated the embodiment of a preferred single sample needle assembly 10. The basic external components of needle assembly 10 include a housing 12, a first needle cannula 14 adapted for insertion into a patient and a second needle cannula 15 at the opposite end of housing 12, the second needle cannula adapted for penetration of an evacuated container 16 for collection of a blood sample. Housing 12 includes a threaded portion 18 adjacent second cannula 15 onto which a container holder 19 is threaded by its internal mating threads 20 at the forward end of the holder. Evacuated container 16 slides into holder 19 so that second needle cannula 15 can penetrate the penetrable stopper 21 at the forward end of the evacuated container. These general aspects of blood sample collection in this type of structure are well known to those skilled in this art.

In FIGS. 2, 3 and 4, the detailed construction of needle assembly 10 is illustrated. Housing 12 has a forward end 24 and a rearward end 25, these ends being preferably separable in order to place a slidable plug 26 in its proper position within the housing. Forward end 24 is preferably cylindrically shaped and has a bore 29 preferably extending partially through this forward end which is generally sized to slidably fit needle cannula 14 therein. In this embodiment being described, since bore 29 does not extend completely through forward end 24, a smaller diameter channel 30 communicates with bore 29 forming an access opening 31 at this end of forward end 24. At the junction between bore 29 and channel 30 a shoulder 33 is formed. Needle cannula 14 abuts against the shoulder 33 for proper positioning. Once the needle cannula is in position it may be suitably affixed such as by adhesive means or the like.

Forward end 24 of the housing also includes a number of longitudinal ribs 28 surrounding the outwardly extending cannula. A needle shield (not shown) generally covers the outwardly extending needle cannula and includes mating internal ribs within. The mating ribs between needle shield and needle assembly allow the user to facilitate the insertion or removal of the needle assembly into tube holder 19. Forward end 24 also includes an annular flange 32 which serves to provide a surface for joining the two portions of the housing together upon assembly. Once again, suitable fastening means, such as adhesives or the like may be used to secure the two portions of the housing together.

Rearward end 25 is also preferably cylindrically shaped and includes a larger bore extending partially into one end of this portion, this end being opposite from the end from which second needle cannula 15 extends. This bore serves as a chamber 40 within housing 12 to be described in greater detail hereinafter. A smaller bore 41 extends through the opposite end of rearward end 25 and is substantially similar to bore 29 in the forward end of the housing. Once again, bore 41 is sized to accept the diameter of second needle cannula 15, which is secured to bore 41 by appropriate means, including adhesives and the like. The outer portion of rearward end 25 surrounding bore 41 includes external threads 18 which are provided as previously mentioned as a connection mechanism to the tube holder. The outer portion 42 of rearward end 25 surrounding chamber 40 is preferably smooth and translucent or transparent so that a user of this assembly can view the interior of the housing. In many situations, it may be preferable to make the entire rearward end, and even possibly the forward end, out of translucent or transparent material for ease of manufacture and to minimize the different types of materials which may be used in this assembly. Translucent rigid plastic is the most desirable material for inclusion in this assembly. Various sealed windows, ports or other means for a user to view the contents of the chamber are within the purview of this invention. It is perferable that such window or port be sealed so that any blood which enters chamber 40 upon the needle entering the vein will not escape from this assembly.

Second needle cannula 15 which extends outwardly from rearward end 25 preferably extends through bore 41 so that it also has an interior portion 44 extending inwardly into chamber 40, sufficiently far so that plug 26 is prevented from becoming disengaged therefrom. Distal end 45 of this hollow needle cannula is sealed closed, such as with a deposit of adhesive material, crimping or the like. Two holes 48 and 49 are located through the side of interior portion 44 of this needle cannula and establish fluid communication between chamber 40 and the lumen of this cannula. These holes are preferably spaced along a substantially axial line on the interior portion of this needle cannula. Rearward end 25 also includes an annular flange 46 which cooperates with flange 32 in joining the two ends of the housing together. Upon assembling forward end and rearward end together with plug 26 placed in its proper position, respective flanges 32 and 46 are secured together by appropriate fastening means, such as adhesives and the like. Plug 26 is placed inside chamber 40 so that it contacts the wall of housing portion 42 surrounding the chamber and also slides along the outer surface of interior portion 44 of the second needle cannula. The spacing between side holes 48 and 49 in this embodiment is greater than the longitudinal length of plug 26 so that only one of these side holes at a time is covered by slidable plug 26. As can be seen more clearly in FIG. 2, which represents needle assembly 10 as it would appear in its initial condition before use, plug 26 initially overlies side hole 49 which is the hole more distal to bore 41 in this rearward end. In general terms, plug 26 is adapted to form a liquid-tight but slidable contact with translucent housing portion 42 surrounding chamber 40 and the outer surface of interior portion 44 of the second needle cannula. The preferred construction of plug 26 is more clearly illustrated by referring to FIGS. 3, 4 and 5, taken in conjunction with FIG. 2.

Plug 26 is illustrated as a composite structure having an outer envelope 51 made from a material which is impermeable to both gas and liquid. Most desirably, this impermeable material is a flexible, elastomeric material, such as natural rubber, silicone rubber and the like. It is preferably cylindrically shaped and includes an annular flange 52 at one end. Flange 52 has an outer diameter which provides a liquid-tight fit against the wall portion of the housing surrounding chamber 40. In this regard, since only flange 52 makes contact with the wall of the housing, and the remaining portion of outer envelope 51 is not in contact with the housing, frictional surface area is minimized to allow this plug to slide more readily under a negative pressure gradient inside chamber 40. As this impermeable material forms an outer envelope in the composite structure, an inner cavity 54 forms the interior portion of this impermeable material, with apertures 55 and 56 at opposite ends of this material communicating with cavity 54. Aperture 55 has a diameter which forms a liquid-tight fit around needle cannula portion 44, while also being slidable thereon. Aperture 56 is preferably somewhat larger in diameter than the needle cannula so that air can pass through this end of the composite plug. Chamber 58 is provided to assist the assembly of the composite plug together. A plurality of openings 59, herein in the form of longitudinal slots, is provided through the peripheral wall of the impermeable material. Although four openings 59 are illustrated, this number may vary, if desired. Openings 59 provide a fluid path between chamber 40 and interior cavity 54 particularly for the flow of air, or other gases, through the composite plug.

A second component of composite plug 26 is a substantially cylindrical member 60 which is permeable to air or other gases, but is impermeable to blood or other liquids. A passageway 61 extends completely through member 60 so that needle cannula portion 44 can be received therethrough. It is not essential that any contact be made between passageway 61 and needle cannula portion 44, although slight contact would be acceptable. However, air-permeable member 60 is received in cavity 54 in the outer envelope in a compression fit so that blood or liquid is prevented from flowing through this composite plug structure. Member 60 may be introduced into cavity 54 through aperture 56, or otherwise, especially due to the flexible nature of the outer envelope material. Although other materials may be used, it is preferred that air-permeable member 60 be made of porous material, such as sintered polyethylene having a general pore rating of about ten (10) microns.

Figure 6:
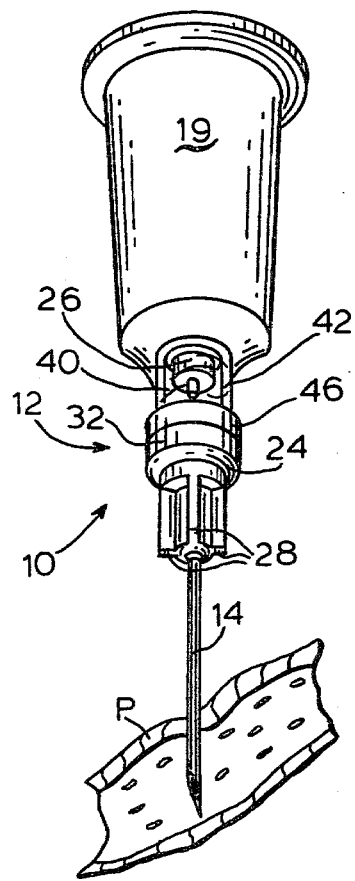
FIG. 6 is a perspective view of the needle assembly connected to a holder and inserted into a patient so that a user can view same for indication of vein entry.

Turning now to FIG. 6, preferred needle assembly 10 is illustrated connected to a collection holder 19. At this stage of the blood collecting procedure, evacuated tube 16 is not yet attached while cannula 14 is initially inserted into patient P. At this stage, plug 26 is positioned inside chamber 40, in liquid-tight contact with the wall surrounding the chamber and interior portion 44 of the second cannula, in the position illustrated in FIG. 2. In this regard, distal side hole 49 is initially covered by the plug, while side hole 48 is uncovered. Also at this stage, since no vacuum is being applied to needle cannula 15, the chamber and needles are substantially at atmospheric pressure conditions, so that there is air in the hollow portions of the needles and the chamber. Once vein entry has been made by needle cannula 14, blood will flow under normal tourniquet pressure through cannula 14 and will fill a forward part 40a of chamber. The air which was in this portion of the chamber is allowed to escape through the plug by passing through holes 59 in the impermeable material and then through the air-permeable member within. Air may enter either side hole 48 or 49 and escape through second needle cannula 15 which is open at its proximal end. As a result, blood may readily fill forward chamber 40a with no air blockage encountered as in prior art devices.

Blood in the forward chamber is prevented from flowing into the second needle cannula due to both the liquid-tight seal formed by the impermeable outer envelope and by the blood impermeability characteristics of the porous member inside the envelope. As a result, blood in the forward chamber can be viewed by a user through translucent portion 42 to have a visual indication that vein entry has been achieved by cannula 14. It should be pointed out that the force of blood flowing into the chamber under normal tourniquet pressure will not be sufficient to make the plug slide away from its initially lying position inside the chamber.

Figure 7:
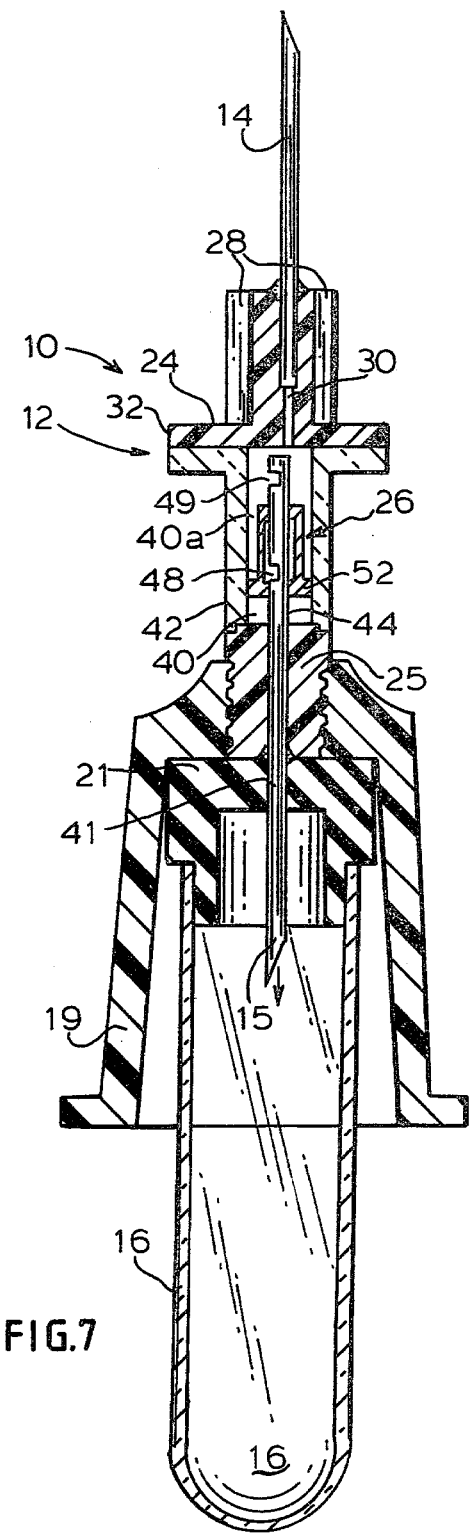
FIG. 7 is a cross-sectional view taken along line 7—7 of FIG. 1 with the components in an assembled condition as they would appear during use.

Once this visual observation of vein entry is confirmed by the user, evacuated tube 16 is then inserted into holder 19 so that penetrable stopper 21 is penetrated by hollow cannula 15. FIG. 7 illustrates this insertion of the evacuated blood collection tube. Once second cannula 15 is into the vacuum area inside container 16, a negative pressure gradient is transmitted into chamber 40 through side hole 48. Under the influence of this negative pressure gradient, plug 26 is drawn toward the source of the negative pressure so that it slides inside the chamber and along interior portion 44 of the second cannula. The effect of this sliding causes side hole 49 to become uncovered, with side hole 48 now becoming covered by the plug. Although FIG. 7 illustrates a complete covering of side hole 48 due to the sliding movement of the plug, only partial covering of this side hole, or perhaps no covering at all, could occur as the vacuum conditions are applied. The significant feature is that distal side hole 49 is uncovered due to the sliding movement of the plug which now results in a free path for blood inside forward chamber 40a to flow into the second needle cannula. Blood will now flow through the needle assembly and into the blood collection container until a sufficient quantity has been collected, whereby the blood sample procedure is terminated by removal of needle cannula 14 from the vein of the patient.

Thus, the needle assembly of the present invention includes a slidable plug which is easily mounted in the assembly and allows air to escape from the assembly during the initial venipuncture step as vein entry is being determined. With this air escapement feature, a blood trace upon vein entry will immediately flow into the chamber of the present needle assembly with a visual indicator feature being provided to the user to take cognizance of vein entry. With this assurance of vein entry, the blood collection container can be satisfactorily filled for collection of the sample from the patient.

What is claimed is:

1. A single sample needle assembly for determining vein entry when collecting a blood sample from a patient into an evacuated container comprising:

a housing having a forward end, a rearward end and a chamber within, said housing being translucent at least around the chamber so that said chamber can be viewed by a user of said assembly;

a first access opening through the forward end of said housing in fluid communication with said chamber;

a first cannula extending outwardly from said first access opening in fluid communication with said chamber adapted for insertion into a patient;

a second access opening through the rearward end of said housing in fluid communication with said chamber;

a second cannula in fluid communication with said second access opening extending inwardly into said chamber with a closed end and a pair of spaced side holes therethrough; and a plug of air-permeable, blood-impermeable material in liquid-tight but slidable contact with said housing surrounding said chamber and said second cannula, said plug initially overlying the side hole more distal to said second access opening while leaving the other side hole uncovered in said chamber whereby blood, but not air, flowing into said chamber from said first cannula under normal tourniquet pressure is prevented by said plug from flowing into said second cannula but can be viewed by a user through said translucent housing to indicate vein entry by said first cannula, said plug adapted to slide under the influence of a negative pressure gradient applied to said second access opening to thereby uncover said distal side hole whereby blood may flow into said chamber, through said distal side hole and through said second cannula for collection out of said second access opening.

2. The assembly of claim 1 wherein the spacing between said side holes is greater than the longitudinal length of said plug so that only one of said side holes at a time is covered by said plug.

3. The assembly of claim 1 wherein only a portion of the peripheral surface of said plug is in liquid-tight contact with said housing surrounding said chamber.

4. The assembly of claim 1 wherein said plug further comprises a material impermeable to both air and blood in a composite relationship with said air-permeable, blood-impermeable material, said impermeable material making liquid-tight contact with said housing surrounding said chamber and said second cannula.

5. The assembly of claim 4 wherein only a portion of the peripheral surface of said impermeable plug material is in liquid-tight contact with said housing surrounding said chamber.

6. The assembly of claim 5 wherein only a portion of the peripheral surface of said impermeable plug material is in liquid-tight contact with said second cannula.

7. The assembly of claim 6 wherein said impermeable material is shaped in an outer envelope around said air-permeable material with at least one opening therethrough so that said air-permeable material is in direct fluid communication with said chamber.

8. The assembly of claim 7 wherein said impermeable material includes a plurality of openings to expose said air-permeable material to direct fluid communication with said chamber.

9. The assembly of claim 4 wherein said impermeable material is flexible.

10. The assembly of claim 9 wherein said impermeable material is elastomeric.

11. The assembly of claim 10 wherein said impermeable material is silicone rubber.

12. The assembly of claim 1 wherein said plug material is in the shape of a hollow cylinder.

13. The assembly of claim 1 wherein said plug material is porous.

14. The assembly of claim 13 wherein said plug material is sintered polyethylene having a general pore rating of about ten (10) microns.

15. The assembly of claim 1 wherein the end of said second cannula inside said chamber is sealed closed with an adhesive.

16. The assembly of claim 1 which further includes a delivery cannula extending outwardly from said second access opening in fluid communication with said second cannula adapted for penetration of an evacuated container for collection of a blood sample.

17. The assembly of claim 16 wherein said delivery cannula and said second cannula are joined together in a unitary, one-piece structure.

18. The assembly of claim 1 wherein the entire housing is translucent.

19. The assembly of claim 1 which further includes a holder for an evacuated container connected to said housing.

20. A single sample needle assembly for determining fluid access when collecting a fluid sample from a source of fluid into a vacuum collection device comprising:
   a housing with a chamber therein and having first and second access means therethrough in fluid communication with said chamber, said housing including means for viewing the contents of the chamber therein, said second access means adapted for fluid communication with said vacuum collection device;
   means extending into said chamber in closed relationship with said second access means except for a pair of holes each spaced along a substantially axial line from said second access means; and
   means for slidably plugging said chamber to prevent liquid from flowing into one of said holes while allowing gas to flow into one of said holes at a first position in said chamber whereby the prevented liquid may be viewed by a user through said viewing means, said slidable means being slidably responsive to a negative pressure gradient at said second access means to allow liquid to flow into one of said holes at a second position in said chamber whereby liquid may be collected from said second access means.

21. A needle assembly for determining fluid access when collecting a fluid sample from a source of fluid into a vacuum collection device comprising:
   a housing with a chamber therein and having first and second access means therethrough in fluid communication with said chamber, said housing including means for viewing the contents of the chamber therein, said second access means adapted for fluid communication with said vacuum collection device;
   means extending into said chamber for directing passage of gas and liquid into said second access means;
   and
   means for operatively plugging said chamber to prevent liquid from flowing into said extension means while allowing gas to flow into said extension means at a first position in said chamber whereby the prevented liquid may be viewed by a user through said viewing means, said operative means being movable to a second position in said chamber to allow liquid to flow into said extension means whereby liquid may be collected from said second access means.

22. A single sample needle assembly for determining vein entry when collecting a blood sample from a patient into an evacuated container comprising:
   a translucent housing having a forward end, a rearward end and a chamber within;
   a first cannula extending outwardly from the forward end of said housing in fluid communication with said chamber adapted for insertion into a patient;
   a second cannula having an exterior portion extending outwardly from the rearward end of said housing adapted for penetration of an evacuated container for collection of a blood sample and having an interior portion extending inwardly into said chamber with a closed end and a pair of spaced side holes therethrough; and
   a composite plug of air-permeable, blood-impermeable material and an elastomeric impermeable material slidably positioned in said chamber with said impermeable material forming an outer envelope around said air-permeable material with a plurality of openings therethrough so that said air-permeable material is in direct fluid communication with said chamber, said impermeable material being in liquid-tight contact with said housing surrounding said chamber and the interior portion of said cannula, said plug being sized with respect to the spacing of said side holes to initially overlie the side hole more distal to said rearward end while leaving the other side hole uncovered inside said chamber whereby blood, but not air, flowing into said chamber from said first cannula under normal tourniquet pressure is prevented by said plug from flowing into said second cannula but can be viewed by a user through said translucent housing to indicate vein entry by said first cannula, said plug adapted to slide under the influence of a negative pressure gradient applied to said second cannula by an evacuated container to thereby uncover said distal side hole whereby blood may flow into said chamber, through said distal side hole and through said second cannula for collection into said evacuated container.

* * * * *